US010647654B2

(12) United States Patent
Bergmeier et al.

(10) Patent No.: US 10,647,654 B2
(45) Date of Patent: May 12, 2020

(54) GLUCOSE TRANSPORT INHIBITORS AND METHODS OF USING SAME

(71) Applicant: OHIO UNIVERSITY, Athens, OH (US)

(72) Inventors: Stephen Bergmeier, Athens, OH (US); Xiaozhuo Chen, Athens, OH (US)

(73) Assignee: Ohio University, Athens, OH (US)

( * ) Notice: Subject to any disclaimer, the term of this patent is extended or adjusted under 35 U.S.C. 154(b) by 0 days.

(21) Appl. No.: 16/311,417

(22) PCT Filed: Jun. 23, 2017

(86) PCT No.: PCT/US2017/039036

§ 371 (c)(1),
(2) Date: Dec. 19, 2018

(87) PCT Pub. No.: WO2017/223473

PCT Pub. Date: Dec. 28, 2017

(65) Prior Publication Data

US 2019/0322613 A1 Oct. 24, 2019

Related U.S. Application Data

(60) Provisional application No. 62/354,479, filed on Jun. 24, 2016.

(51) Int. Cl.
*C07C 63/33* (2006.01)
*C07C 39/15* (2006.01)
*C07C 63/331* (2006.01)
*A61P 35/00* (2006.01)

(52) U.S. Cl.
CPC ............ *C07C 63/331* (2013.01); *A61P 35/00* (2018.01); *C07C 39/15* (2013.01)

(58) Field of Classification Search
CPC .............................. C07C 63/331; C07C 39/15
See application file for complete search history.

(56) References Cited

U.S. PATENT DOCUMENTS

| | | | |
|---|---|---|---|
| 4,426,332 | A | 1/1984 | Thoemel et al. |
| 5,407,954 | A | 4/1995 | Freedman et al. |
| 7,105,554 | B2 | 9/2006 | Orchard et al. |
| 9,181,162 | B2 | 11/2015 | Chen et al. |
| 10,000,443 | B2 | 6/2018 | Chen et al. |
| 10,385,005 | B2 | 8/2019 | Chen et al. |
| 2004/0232393 | A1 | 11/2004 | Do et al. |
| 2009/0311249 | A1 | 12/2009 | Gianni et al. |

FOREIGN PATENT DOCUMENTS

WO 2011119866 A1 9/2011

OTHER PUBLICATIONS

Cancer [online], [retrieved on Jul. 6, 2007]. Retrieved from the internet, URL http://www.nlm.nih.gov/medlineplus/cancer.html>.*
Science (1999), vol. 286, 531-537.*
Cancer and Metastasis Reviews (1998), 17(1), 91-106.*
Cui et al., CAS STN Abstract, publ. 2007.
Effenberger et al., CAS STN Abstract CAS RN# 128924-03-8; RN# 128924-04-9, publ. 1991.
Matsumoto et al., Journal of Medicinal Chemistry, 1977, American Chemical Society, vol. 20, No. 1, pp. 17-24.
Youssefyeh et al., Journal of Medicinal Chemistry, 1990, American Chemical Society, vol. 33, pp. 1186-1194.
International Search Report and Written Opinion for PCT/US2017/039036 dated Sep. 29, 2017.
Bahr et al., "Dendritic, 1,1'-binaphthalene-derived cleft-type receptors (Dendroclefts) for the molecular recognition of pyranosides," Hevletica Chimica Acta (2000), vol. 83, No. 7, pp. 1346-1376.
Bauer, et al., "ATP citrate lyase is an important component of cell growth and transformation", Oncogene, (2005), vol. 24, No. 41, pp. 6314-6322.
Beger et al., World Journal of Surgery (2003), Societe Internationale de Chirurgie, vol. 27, pp. 1075-1084.
Belaid et al., Journal of Inorganic Biochemistry (2008), vol. 102, pp. 63-69.
Bergmeier, et al. "Inhibitors of basal glucose transport as anticancer agents," Abstract No. MEDI 363, American Chemical Society, Division of Medicinal Chemistry, Scientific Abstracts for the 239th National Meeting and Exposition, Mar. 21-25, 2010, San Francisco, CA, published Feb. 22, 2010.
Boehm, et al., "Antiangiogenic therapy of experimental cancer does not induce acquired drug resistance," Nature, (1997), vol. 390, pp. 404-407.
Browder, et al., "Antiangiogenic scheduling of chemotherapy improves efficacy against experimental drug-resistant cancer," Cancer Res., (2000), vol. 60, pp. 1878-1886.
Burt, et al., "Using Positron Emission Tomography with [18F]FDG to Predict Tumor Behavior in Experimental Colorectal Cancer", Neoplasia, (2001), vol. 3, No. 3, pp. 189-195.
Cairns, et al., "Metabolic targeting of hypoxia and HIF1 in solid tumors can enhance cytotoxic chemotherapy", Proc. Natl. Acad. Sci. U.S.A., (2007), vol. 104, No. 22, pp. 9445-9450.
Chabner et al., Nature Reviews Cancer (2005), Nature Publishing Group, vol. 5, pp. 65-72.
Chan, et al., "Targeting GLUT1 and the Warburg Effect in Renal Cell Carcinoma by Chemical Synthetic Lethality," Science Translational Medicine, (Aug. 3, 2011), vol. 3, 94ra70, pp. 1-9.
Effenberger et al., "Nucleophile Substitution von Nitrit in Nitrobenzolen, Nitrobiphenylen and Nitronaphtalien," Chemische Berichte, VCH, vol. 124, pp. 163-173 (Jan. 1, 1990).
Elstrom, et al., "Akt stimulates aerobic glycolysis in cancer cells", Cancer Res., (2004), vol. 64, pp. 3892-3899.
Fantin, et al., "Attenuation of LDH-A expression uncovers a link between glycolysis, mitochondrial physiology, and tumor maintenance", Cancer Cell, (Jun. 13, 2006), vol. 9, No. 6, pp. 425-434.

(Continued)

*Primary Examiner* — Shawquia Jackson
(74) *Attorney, Agent, or Firm* — Calfee, Halter & Griswold LLP

(57) ABSTRACT

Compounds that inhibit or reduce glucose transport and methods of using the compounds to treat cancer are provided herein.

19 Claims, No Drawings

(56) References Cited

OTHER PUBLICATIONS

Fantin, et al. "Mitochondriotoxic compounds for cancer therapy", Oncogene, (2006), vol. 25, pp. 4787-4797.
Folkman, et al., "Cancer without disease," Nature, (2004), vol. 427, p. 787.
Gatenby, et al., "Why do cancers have high aerobic glycolysis?", Nat. Rev. Cancer, (2004), vol. 4, pp. 891-899.
Gottlieb, E. "What Does Bioenergetics Have to Do with Cancer?" Am. Assoc. Cancer Res. Edu. Book, (2006), pp. 341-344.
Gottschalk, et al., "Conversion between two cytochalasin B-binding states of the human GLUT1 glucose transporter," Eur. J. Biochem., (2000), vol. 267, pp. 6875-6882.
Herman, et al., "Glucose transport and sensing in the maintenance of glucose homeostasis and metabolic harmony," J. Clin. Invest., (2006), vol. 116, pp. 1767-1775.
Higashi, et al., "FDG Uptake, GLUT-1 Glucose Transporter and Cellularity in Human Pancreatic Tumors", J. Nucl. Med., (1998), vol. 39, No. 10, pp. 1727-1735.
Kagwanja et al., CAS STN Abstracts, Polyhedron (1994), vol. 13, No. 18, pp. 2615-2627.
Katagiri, et al., "Role of tryptophan-388 GLUT1 glucose transporter in glucose-transport activity and photo-affinity labelling with forskolin," Biochem. J., (1993), vol. 291, pp. 861-867.
Kim, et al., "Cancer's molecular sweet tooth and the Warburg effect", Cancer Res., (2006), vol. 66, pp. 8927-8930.
Klein, et al., "Antidiabetes and anti-obesity activity of Lagerstroemia speciosa," Evidence-Based Complementary and Alternative Medicine, (2007), vol. 4, pp. 401-407.
Ko, et al., "Advanced cancers: eradication in all cases using 3-bromopyruvate therapy to deplete ATP", Biochem. Biophys. Res. Commun., (2004), vol. 324, No. 1, pp. 269-275.
Krupka, R. M. "Asymmetrical Binding of Phloretin to the Glucose Transport System of Human Erythrocytes," The Journal of Membrane Biology, (1985), vol. 83, Nos. 1-2, pp. 71-80.
Leaf, Clifton. "The War on Cancer," Fortune (Mar. 9, 2004), Time Inc., pp. 1-13.
Liu, et al. "Small compound inhibitors of basal glucose transport inhibit cell proliferation and induce apoptosis in cancer cells via glucose-deprivation-like mechanisms", Cancer Lettters, (2010), vol. 298, pp. 176-185.
Liu et al. "A small-molecule inhibitor of glucose transporter 1 downregulates glycoloysis, induces cell-cycle arrest, and inhibits cancer cell growth in vitro and in vivo," Molecular Cancer Therapeutics (2012), vol. 11, pp. 1672-1682.
Majumdar et al., "Palladium Mediated bis- and tris-biaryl Heck Coupling for the Synthesis of Heterocycles," Tetrahedron Letters (May 19, 2008), vol. 49, No. 21, pp. 3419-3422.
Ramanathan, et al., "Perturbational profiling of a cell-line model of tumorigenesis by using metabolic measurements", Proc. Natl. Acad. Sci. U.S.A., (2005), vol. 102, No. 17, pp. 5992-5997.
Rastogi, et al., "Glut-1 antibodies induce growth arrest and apoptosis in human cancer cell lines", Cancer Lett., (2007), vol. 257, pp. 244-251.
Ren, et al., "Evidence from transgenic mice that glucose transport is rate-limiting for glycogen deposition and glycolysis in skeletal muscle," J. Biol. Chem., (1993), vol. 268, pp. 16113-16115.
Saito, et al., "Chemical genomics identifies the unfolded protein response as a target for selective cancer cell killing luring glucose deprivation", Cancer Res., (2009), vol. 69, pp. 4225-4234.
Sala et al., "Depsidone Synthesis. Part 16. Benzophenone-Grisa-3'5'-Diene-2'3'-Depsidone Interconversion: A New Theory of Depsidone Biosynthesis," Journal of the Chemical Society, Perkin Transactions 1, Chemical Society, Letchworth, GB; (1981), No. 3, pp. 855-869.
Semenza, G., "Intratumoral hypoxia, radiation resistance, and HIF-1," Cancer Cell, (2004), vol. 5, pp. 405-406.
Smith et al., "Two step synthesis of C2 symmetric 2,6-diarylalkyloxybenzaldehydes—a Mitsunobu approach," Tetrahedron: Asymmetry (1997), vol. 8. No. 20, pp. 3415-3420.
Tobak, "Construction of the 3D Structure of the MTOR Kinase-Domain and Discovery of Novel MTOR Inhibitors", Doctoral Thesis, Rutgers: The State University of New Jersey, (2007), pp. 1-95.
Ulanovskaya, et al., "A Pairwise Chemical Genetic Screen Identifies New Inhibitors of Glucose Transport," Chemistry and Biology, (Feb. 25, 2011), vol. 18, No. 2, pp. 222-230.
Vera, et al., "Genistein Is a Natural Inhibitor of Hexose and Dehydroascorbic Acid Transport through the Glucose Transporter, GLUT1," The Journal of Biological Chemistry, (Apr. 12, 1996), vol. 271, No. 15, pp. 8719-8724.
Wood, et al., "A novel inhibitor of glucose uptake sensitizes cells to FAS-induced cell death", Molecular Cancer Therapeutics, (2008), vol. 7, pp. 3546-3555.
Younes, et al., "Overexpression of the human erythrocyte glucose transporter occurs as a late event in human colorectal carcinogenesis and is associated with an increased incidence of lymph node metastases," Clin. Cancer Res., (1996), vol. 2, pp. 1151-1154.
Yu, et al., "Apoptosis-inducing factor mediates poly(ADP-ribose) (PAR) polymer-induced cell death", Proc. Natl. Acad. Sci. USA, (2006), vol. 103, pp. 18314-18319.
Zhang, Weihe. "Design and Synthesis of Potential Anticancer Agents," Nov. 2010, XP055074386; retrieved from the Internet: URL: https://etd.ohiolink.edu/ap:10:0::NO:10:P10_ACCESSION_NUM:ohiou1288896777.
Zhang, et al. "Inhibitors of basal glucose transport as anticancer agents," American Chemical Society 239th National Meeting & Exposition, Mar. 21-25, 2010, San Francisco, CA, Poster Presentation made on Mar. 24, 2010.
Zhang, et al. "Novel inhibitors of basal glucose transport as potential anticancer agents", Bioorganic and Medicinal Chemistry Letters, (2010), vol. 20, pp. 2191-2194.
Zhou, et al. "Akt substrate TBC1 D1 regulates GLUT1 expression through the mTOR pathway in 3T3-L1 adipocytes", Biochemical Journal, (2008), vol. 411, pp. 647-655.

* cited by examiner

GLUCOSE TRANSPORT INHIBITORS AND METHODS OF USING SAME

CROSS-REFERENCE TO RELATED APPLICATIONS

This application is the U.S. national stage entry of PCT/US2017/039036, filed Jun. 23, 2017, which claims priority to and any other benefit of U.S. Provisional Patent Application No. 62/354,479, filed Jun. 24, 2016, the entire contents of which are fully incorporated by reference herein.

FIELD

The present disclosure relates to chemical compounds that inhibit or reduce glucose transport and methods of using the chemical compounds to treat cancer.

BACKGROUND

The Warburg effect, or upregulated glycolysis, is a near-universal hallmark of cancer cells. Because of the increasing demands for biomaterials and energy generated during rapid cell proliferation, cancer cells rely on upregulating glycolysis. As a result, cancer cells are much more sensitive to changes in glucose concentration and glucose metabolism than normal cells.

Basal glucose transporters (GLUTs) function as glucose channels and are required for maintaining the basic glucose needs of cells. These GLUTs are constitutively expressed and functional in cells and are not regulated by (or sensitive to) insulin. All cells use both glycolysis and oxidative phosphorylation in mitochondria but rely overwhelmingly on oxidative phosphorylation when oxygen is abundant, switching to glycolysis at times of oxygen deprivation (hypoxia), as occurs in cancer. In glycolysis, glucose is converted to pyruvate and 2 ATP molecules are generated in the process. Cancer cells, because of their faster proliferation rates, are predominantly in a hypoxic (low oxygen) state. Therefore, cancer cells use glycolysis (lactate formation) as their predominant glucose metabolism pathway. Such a glycolytic switch not only gives cancer higher potentials for metastasis and invasiveness, but also increases cancer's vulnerability to external interference in glycolysis since cancer cells are "addicted" to glucose and glycolysis. The reduction of basal glucose transport is likely to restrict glucose supply to cancer cells, leading to glucose deprivation that forces cancer cells to slow down growth or to starve.

SUMMARY

Disclosed herein are chemical compounds that inhibit or reduce glucose transport and methods of using the chemical compounds to treat cancer. By way of example to illustrate various aspects of the present disclosure, several exemplary embodiments of chemical compounds and methods of using the chemical compounds to treat cancer are provided herein.

In one exemplary embodiment, compounds according to formula (I), enantiomers thereof, or salts thereof that inhibit or reduce glucose transport are provided:

Formula (I)

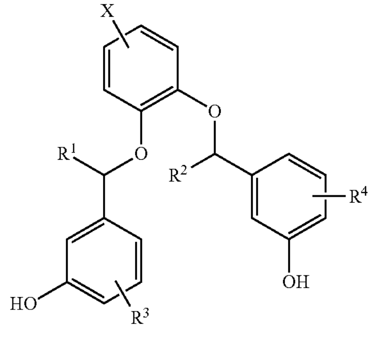

wherein X is selected from the group consisting of: hydrogen; halogen; —O-alkyl; azido (—$N_3$); hydroxyl (—OH); cyano (—CN); nitro (—$NO_2$); and methoxycarbonyl (—$CO_2Me$);

wherein $R^1$ and $R^2$ are independently selected from the group consisting of: hydrogen;

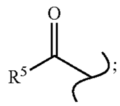;
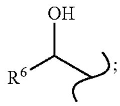; and
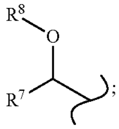;

wherein $R^3$ and $R^4$ are independently selected from the group consisting of: hydrogen; halogen; alkyl; —O-alkyl; hydroxyl (—OH); cyano (—CN); and methoxycarbonyl (—$CO_2Me$);

wherein one of $R^1$ and $R^2$ is hydrogen;

wherein $R^5$ is selected from the group consisting of: hydroxyl (—OH); —O-alkyl; —NH-alkyl; and —N-$(alkyl)_2$;

wherein $R^6$ is selected from the group consisting of: hydrogen; alkyl; and aryl;

wherein $R^7$ is selected from the group consisting of: alkyl; aryl; and heteroaryl; and wherein $R^8$ is selected from the group consisting of: alkyl; aryl; and heteroaryl.

In one exemplary embodiment, compounds according to formula (II), enantiomers thereof, or salts thereof that inhibit or reduce glucose transport are provided:

Formula (II)

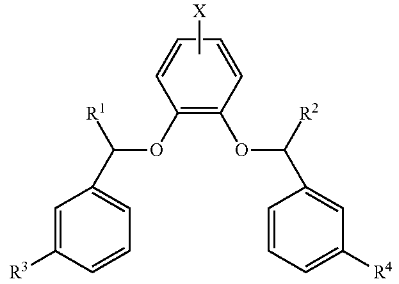

wherein X is selected from the group consisting of: hydrogen; halogen; —O-alkyl; hydroxyl (—OH); cyano (—CN); azido (—$N_3$); nitro (—$NO_2$); and methoxycarbonyl (—$CO_2Me$);

wherein $R^1$ and $R^2$ are independently selected from the group consisting of: hydrogen; hydroxymethyl (—$CH_2OH$); and methoxycarbonyl (—$CO_2Me$);

wherein one of $R^1$ and $R^2$ is hydrogen;

wherein when $R^1$ is hydrogen, $R^3$ is hydroxyl (—OH) and $R^4$ is —O-alkyl; and wherein when $R^2$ is hydrogen, $R^3$ is —O-alkyl and $R^4$ is hydroxyl (—OH).

In one exemplary embodiment, a method of treating cancer in a subject is provided. The method includes administering to a subject in need of such treatment a therapeutically effective amount of: a compound according to formula (I), or a compound according to formula (II), or a combination of a compound according to formula (I) and a compound according to formula (II).

DETAILED DESCRIPTION

The present disclosure is directed to chemical compounds that inhibit or reduce glucose transport and methods of using the chemical compounds to treat cancer. While various exemplary embodiments of compounds and methods are described herein in detail, these embodiments are provided so that the present disclosure will be thorough and complete and will fully convey the scope of the invention to those skilled in the art. It will be understood that the exemplary embodiments described herein are not intended to limit the claims.

The terminology as set forth herein is for description of the embodiments only and should not be construed as limiting the disclosure as a whole. As used in the description and the appended claims, the singular forms “a,” “an,” and “the” are intended to include the plural forms as well, unless the context clearly indicates otherwise. All references to singular characteristics or limitations of the present disclosure shall include the corresponding plural characteristic or limitation, and vice versa, unless otherwise specified or clearly implied to the contrary by the context in which the reference is made. All materials incorporated by reference are incorporated in their entirety unless otherwise stated. Unless otherwise indicated (e.g., by use of the term “precisely”), all numbers expressing quantities, properties such as molecular weight, reaction conditions, and so forth as used in this disclosure are to be understood as being modified in all instances by the term “about.” Accordingly, unless otherwise indicated, the numerical properties set forth in this disclosure are approximations that may vary depending on the desired properties sought to be obtained in the embodiments described herein.

The term “alkyl” refers to a straight- or branched-chain alkyl group having from 1 to 20 carbon atoms in the chain. For example, the alkyl group can be a $(C_1\text{-}C_{20})$alkyl, a $(C_1\text{-}C_{12})$alkyl, a $(C_1\text{-}C_8)$alkyl, a $(C_1\text{-}C_6)$alkyl, or a $(C_1\text{-}C_4)$ alkyl. Exemplary alkyl groups include, but are not limited to, methyl (Me), ethyl (Et), n-propyl, isopropyl, butyl, isobutyl, sec-butyl, tert-butyl (tBu), pentyl, isopentyl, tert-pentyl, hexyl, and isohexyl.

The term “aryl” refers to a functional group derived from a simple aromatic ring compound where one hydrogen atom is removed from the ring. Exemplary aryl groups include, but are not limited to, phenyl; naphthyl; indanyl; indenyl; 2-, 3-, and 4-hydroxyphenyl; 2,3-, 2,4-, 2,5-, 2,6-, 3,4-, and 3,5-dihydroxyphenyl; 2,3,4-, 2,3,5-, 2,3,6-, and 3,4,5-trihydroxyphenyl; 2,3,4,5- and 2,3,4,6-tetrahydroxyphenyl; perhydroxyphenyl; 2, 3, and 4-halophenyl; 2, 3, and 4-alkylphenyl; 2, 3, and 4-cyanophenyl; 2, 3, and 4-ketophenyl; 2, 3, and 4-carboxyphenyl; 2, 3, and 4-aminophenyl; 2, 3, and 4-nitrophenyl; 2, 3, and 4-hydroxyphenyl; 2, 3, and 4-alkoxyphenyl; disubstituted phenyl, and trisubstituted phenyl derivatives.

The term “heteroaryl” refers to a functional group derived from a heteroaromatic ring. Heteroaromatic species contain a heteroatom, or an atom other than hydrogen or carbon, including, oxygen, nitrogen, sulfur, phosphorous, silicon, and boron. Exemplary heteroaryl groups include, but are not limited to, furans, benzofurans, thiophenes, benzothiophenes, pyrroles, indoles, and borabenzenes.

The term “O-alkyl” refers to an alkyl group singly bonded to an oxygen, or an aryl group singly bonded to an oxygen. Exemplary O-alkyl groups include, but are not limited to, methoxy (OMe), ethoxy, n-propoxy, i-propoxy, n-butoxy, t-butoxy, and phenoxy.

The term “salt” refers to an ionic species resulting from the pairing of an anionic derivative of one of the compounds of formula (I) and formula (II) with a cationic species. The cationic species may include, but is not limited to, lithium, sodium, potassium, magnesium, calcium, and manganese.

The term “therapeutically effective” when used to describe an amount of a compound administered in a method, refers to the amount of a compound that achieves the desired biological effect, for example, an amount that leads to the inhibition or reduction of basal glucose transport.

In one exemplary embodiment, compounds according to formula (I), enantiomers thereof, or salts thereof that inhibit or reduce glucose transport are provided:

Formula (I)

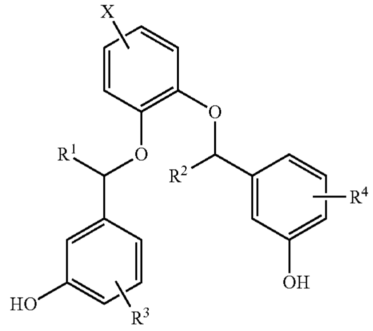

wherein X is selected from the group consisting of: hydrogen; halogen; —O-alkyl; azido ($—N_3$); hydroxyl (—OH); cyano (—CN); nitro ($—NO_2$); and methoxycarbonyl ($—CO_2Me$);

wherein $R^1$ and $R^2$ are independently selected from the group consisting of: hydrogen;

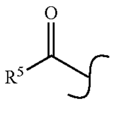 ; 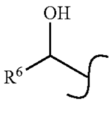 ; and 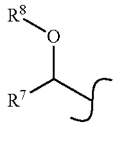 ;

wherein $R^3$ and $R^4$ are independently selected from the group consisting of: hydrogen; halogen; alkyl; —O-alkyl; hydroxyl (—OH); cyano (—CN); and methoxycarbonyl ($—CO_2Me$);

wherein one of $R^1$ and $R^2$ is hydrogen;

wherein $R^5$ is selected from the group consisting of: hydroxyl (—OH); —O-alkyl; —NH-alkyl; and $—N(alkyl)_2$;

wherein $R^6$ is selected from the group consisting of: hydrogen; alkyl; and aryl;

wherein $R^7$ is selected from the group consisting of: alkyl; aryl; and heteroaryl and wherein $R^8$ is selected from the group consisting of: alkyl; aryl; and heteroaryl.

In certain embodiments, compounds according to formula (I), enantiomers thereof, or salts thereof are provided, wherein:

X is halo;

$R^1$ is hydrogen;

$R^2$ is

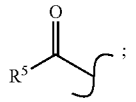

$R^3$ is hydrogen;

$R^4$ is hydrogen; and $R^5$ is —O-alkyl.

In certain embodiments, a compound according to formula (I), referred to herein as EKB-1, is provided, wherein:

X is —Cl;

$R^1$ is hydrogen;

R2 is

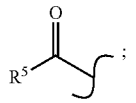

R3 is hydrogen;

R4 is hydrogen; and

R5 is methoxy (—OMe).

The structure of EKB-1 is shown below.

EKB-1

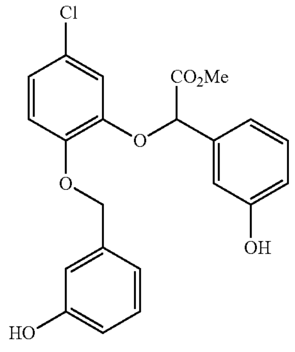

In certain embodiments, compounds according to formula (I), enantiomers thereof, or salts thereof are provided, wherein:

X is halo;

$R^1$ is

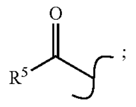

$R^2$ is hydrogen;

$R^3$ is hydrogen;

$R^4$ is hydrogen; and $R^5$ is —O-alkyl.

In certain embodiments, a compound according to formula (I), referred to herein as EKB-2, is provided, wherein:

X is —Cl;

$R^1$ is

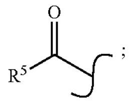

$R^2$ is hydrogen;

$R^3$ is hydrogen;

$R^4$ is hydrogen; and $R^5$ is methoxy (—OMe).

The structure of EKB-2 is shown below.

EKB-2

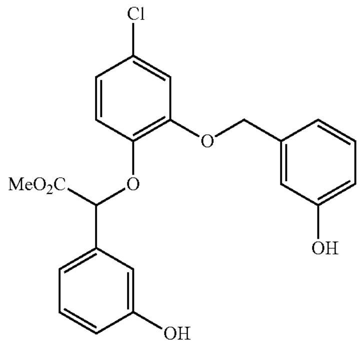

In certain embodiments, compounds according to formula (I), enantiomers thereof, or salts thereof are provided, wherein:

X is halo;

$R^1$ is

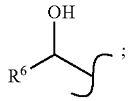

$R^2$ is hydrogen;

$R^3$ is hydrogen;

$R^4$ is hydrogen; and $R^6$ is hydrogen.

In certain embodiments, a compound according to formula (I), referred to herein as EKB-3, is provided, wherein:

X is —Cl;

$R^1$ is

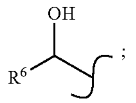

$R^2$ is hydrogen;

$R^3$ is hydrogen;

$R^4$ is hydrogen; and $R^6$ is hydrogen.

The structure of EKB-3 is shown below.

EKB-3

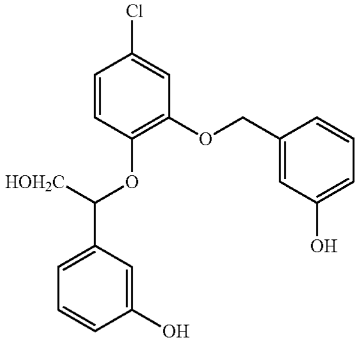

In certain embodiments, compounds according to formula (I), enantiomers thereof, or salts thereof are provided, wherein:

X is halo;

$R^1$ is hydrogen;

$R^2$ is

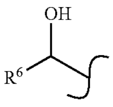 ;

$R^3$ is hydrogen;

$R^4$ is hydrogen; and $R^6$ is hydrogen.

In certain embodiments, a compound according to formula (I), referred to herein as EKB-4, is provided, wherein:

X is —Cl;

$R^1$ is hydrogen;

$R^2$ is

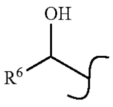 ;

$R^3$ is hydrogen;

$R^4$ is hydrogen; and $R^6$ is hydrogen.

The structure of EKB-4 is shown below.

EKB-4

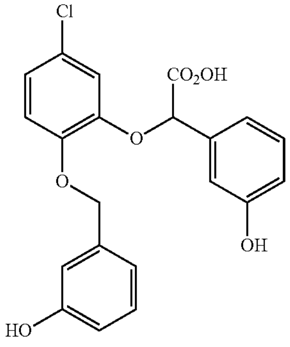

In one exemplary embodiment, compounds according to formula (II), enantiomers thereof, or salts thereof that inhibit or reduce glucose transport are provided:

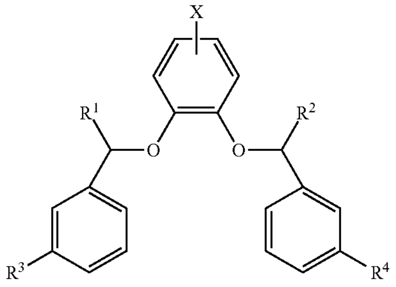

wherein X is selected from the group consisting of: hydrogen; halogen; —O-alkyl; hydroxyl (—OH); cyano (—CN); azido (—$N_3$); nitro (—$NO_2$); and methoxycarbonyl (—$CO_2Me$);

wherein $R^1$ and $R^2$ are independently selected from the group consisting of: hydrogen; hydroxymethyl (—$CH_2OH$); and methoxycarbonyl (—$CO_2Me$);

wherein one of $R^1$ and $R^2$ is hydrogen;

wherein when $R^1$ is hydrogen, $R^3$ is hydroxyl (—OH) and $R^4$ is —O-alkyl; and wherein when $R^2$ is hydrogen, $R^3$ is —O-alkyl and $R^4$ is hydroxyl (—OH).

In certain embodiments, compounds according to formula (II), enantiomers thereof, or salts thereof are provided, wherein:

X is halo;

$R^1$ is hydrogen;

$R^2$ is methoxycarbonyl (—$CO_2Me$);

$R^3$ is hydroxyl (—OH); and $R^4$ is —O-alkyl.

In certain embodiments, a compound according to formula (II), referred to herein as JDB-1, is provided, wherein:

X is —Cl;

$R^1$ is hydrogen;

$R^2$ is methoxycarbonyl (—$CO_2Me$);

$R^3$ is hydroxyl (—OH); and $R^4$ is methoxy (—OMe).

The structure of JDB-1 is shown below.

JDB-1

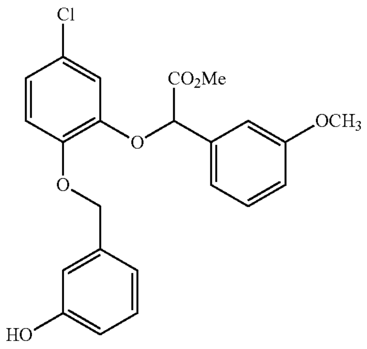

In certain embodiments, compounds according to formula (II), enantiomers thereof, or salts thereof are provided, wherein:

X is halo;

$R^1$ is hydrogen;

$R^2$ is hydroxymethyl (—$CH_2OH$);

$R^3$ is hydroxyl (—OH); and $R^4$ is —O-alkyl.

In certain embodiments, a compound according to formula (II), referred to herein as JDB-2, is provided, wherein:

X is —Cl;

$R^1$ is hydrogen;

$R^2$ is hydroxymethyl (—$CH_2OH$);

$R^3$ is hydroxyl (—OH); and $R^4$ is methoxy (—OMe).

The structure of JDB-2 is shown below.

JDB-2

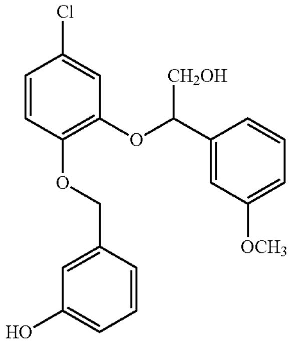

In one exemplary embodiment, compounds according to formula (I) and formula (II), and in particular, compounds EKB-1, EKB-2, EKB-3, EKB-4, JDB-1, and JDB-2, are prepared according to the following reaction schemes.

SCHEME 1

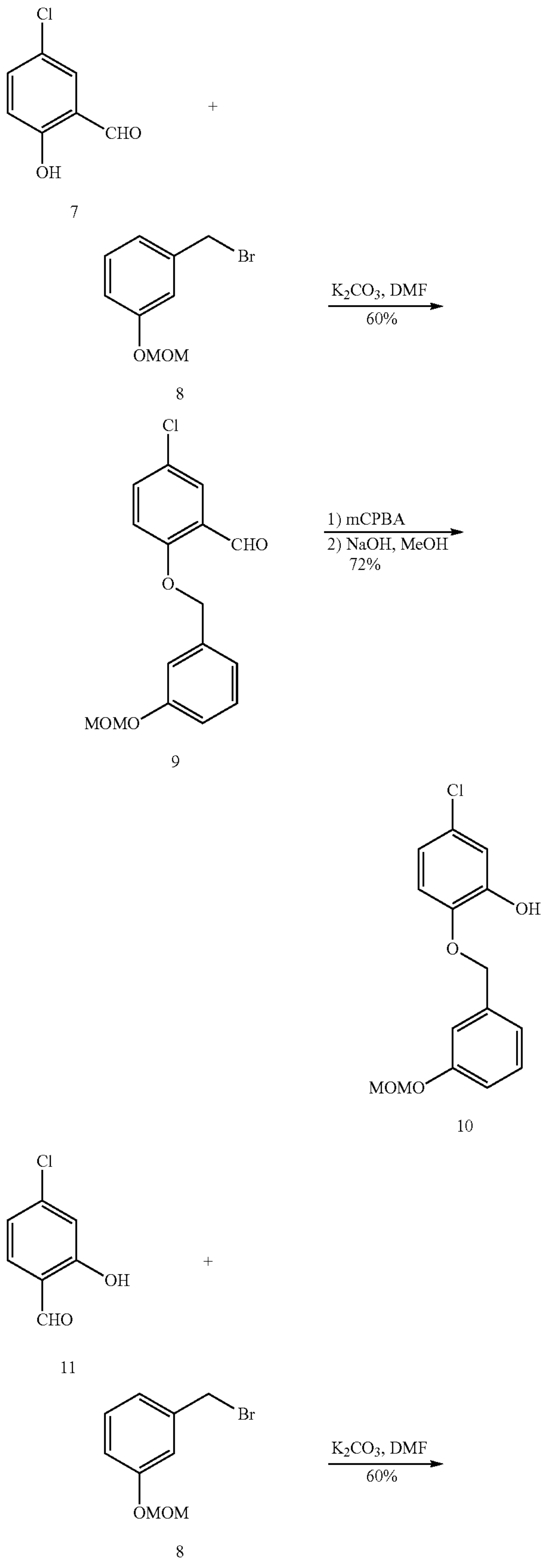

-continued

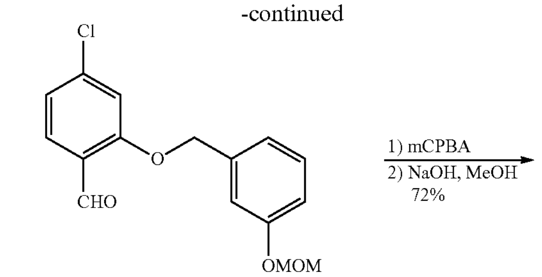

12

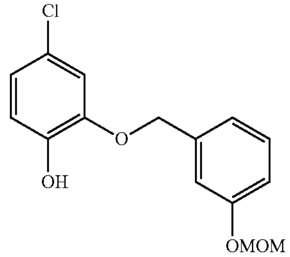

13

As seen in Scheme 1, two different monoalkylated phenols (10) and (13) were prepared. Commercially available 5-chlorosalicylaldehyde (7) and 4-chlorosalicylaldehyde (11) were alkylated with benzyl bromide (8) to provide compounds (9) and (12), respectively. A Baeyer-Villiger reaction followed by hydrolysis of the resulting formate ester provided the monoalkylated phenol compounds (10) and (13).

After preparing monoalkylated phenol compounds (10) and (13), the synthesis of a substituted derivative was carried out. As seen in Scheme 2, ester (14) was protected as a MOM-ether and the benzylic position was brominated using NBS to provide compound (16) in excellent yield.

SCHEME 2

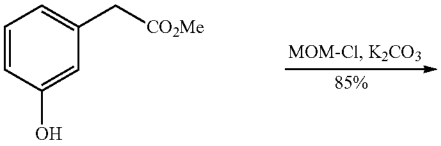

14

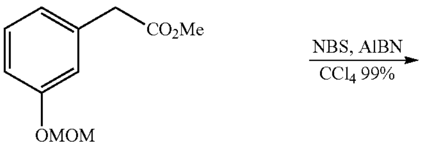

15

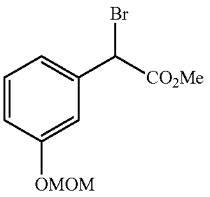

16

As seen in Scheme 3, alkylation of compound (10) with compound (16) provided compound (17) in moderate yield. Removal of the MOM-protecting groups provided compound EKB-1. Reduction of the ester followed by removal of the MOM-protecting groups provided compound EKB-4.

SCHEME 3

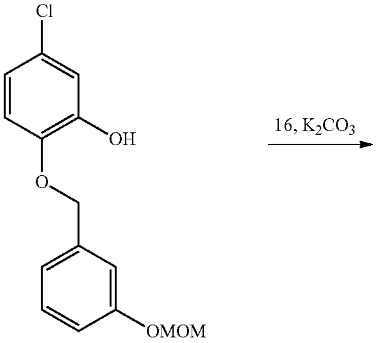

10

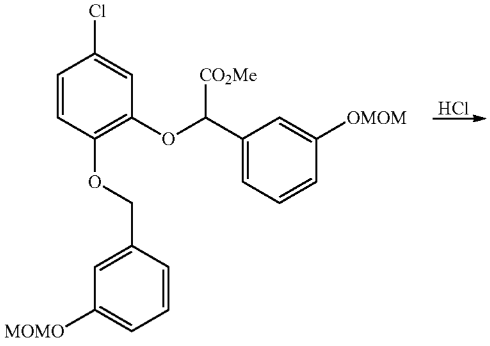

17

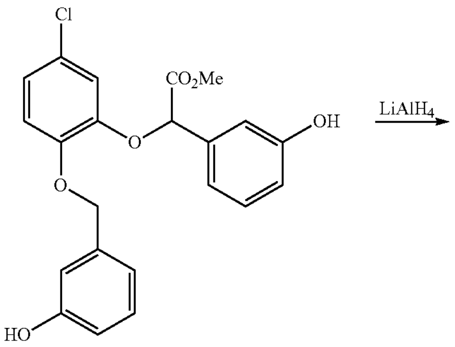

EKB-1

-continued

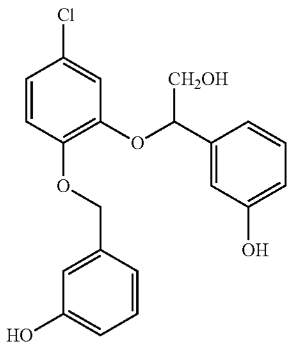

EKB-4

-continued

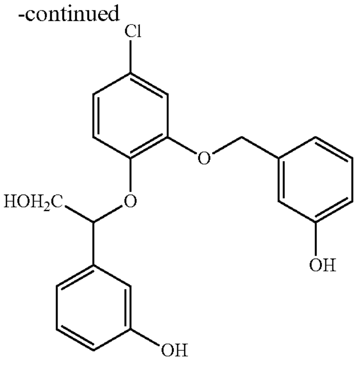

EKB-3

Compounds EKB-2 and EKB-3 were prepared in the same way starting with phenol (13), as shown in Scheme 4.

SCHEME 4

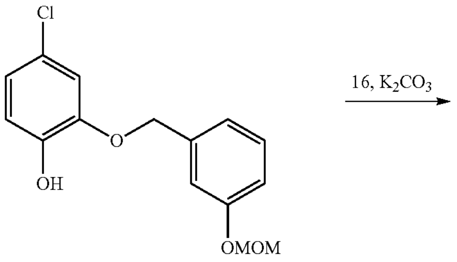

13

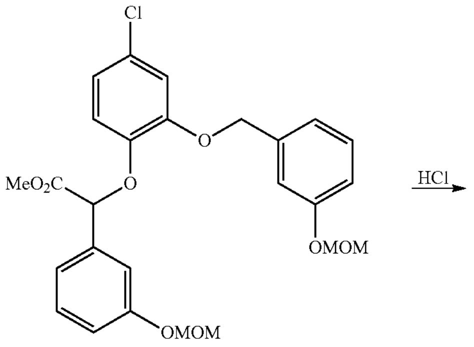

18

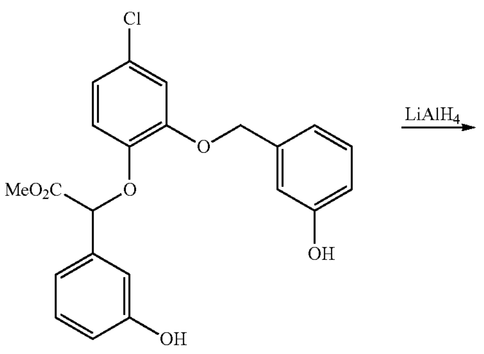

EKB-2

Compounds JDB-1 and JDB-2 were prepared by the same methods used to prepare the EKB compounds.

In certain exemplary embodiments, analogs of EKB-compounds, enantiomers thereof, or salts thereof are provided. In certain exemplary embodiments, analogs of EKB-compounds, enantiomers thereof, or salts thereof according to formula (A) are provided:

Formula (A)

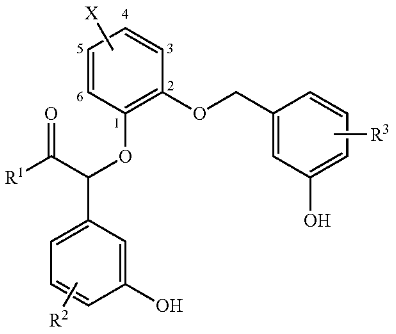

wherein X is selected from the group consisting of: halogen; cyano (—CN); azido (—$N_3$); nitro (—$NO_2$); —O-alkyl; hydroxyl (—OH); and methoxycarbonyl (—$CO_2Me$);

wherein $R^1$ is selected from the group consisting of: hydroxyl (—OH); —O-alkyl; —NH-alkyl; —N(alkyl)$_2$; and wherein $R^2$ and $R^3$ are independently selected from the group consisting of: alkyl; —O-alkyl; hydroxyl (—OH); halogen; cyano (—CN); and methoxycarbonyl (—$CO_2Me$).

In certain exemplary embodiments, analogs of EKB-compounds, enantiomers thereof, or salts thereof according to formula (B) are provided:

Formula (B)

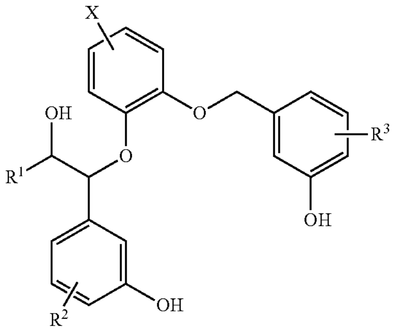

wherein X is selected from the group consisting of: halogen; cyano (—CN); azido (—$N_3$); nitro (—$NO_2$); —O-alkyl; hydroxyl (—OH); and methoxycarbonyl (—$CO_2Me$);

wherein $R^1$ is selected from the group consisting of: alkyl and aryl; and wherein $R^2$ and $R^3$ are independently selected from the group consisting of: alkyl; —O-alkyl; hydroxyl (—OH); halogen; cyano (—CN); and methoxycarbonyl (—$CO_2Me$).

In certain exemplary embodiments, analogs of EKB-compounds, enantiomers thereof, or salts thereof according to formula (C) are provided:

Formula (C)

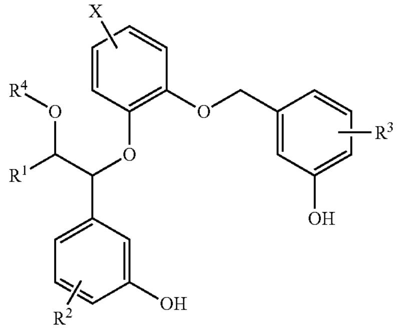

wherein X is selected from the group consisting of: halogen; cyano (—CN); azido (—$N_3$); nitro (—$NO_2$); —O-alkyl; hydroxyl (—OH); and methoxycarbonyl (—$CO_2Me$);

wherein $R^1$ is selected from the group consisting of: alkyl and aryl; and wherein $R^2$ and $R^3$ are independently selected from the group consisting of: alkyl; —O-alkyl; hydroxyl (—OH); halogen; cyano (—CN); and methoxycarbonyl (—$CO_2Me$).

Compounds EKB-1, EKB-2, EKB-3, EKB-4, JDB-1, and JDB-2 were assayed for their ability to inhibit glucose uptake and cell growth in A549 lung cancer cell lines. A standard glucose uptake assay may be used to evaluate glucose uptake inhibition, and an MTT cell proliferation assay may be used to evaluate cancer cell growth inhibition. As seen in Table 1, compounds EKB-1, EKB-2, EKB-3, EKB-4, JDB-1, and JDB-2 inhibited basal glucose transport in A549 cells by 54.3%, 56.1%, 62.8%, 77.8%, 19.7%, and 34.8%, respectively, as measured by a standard glucose uptake assay. DMSO treated cells served as the negative control. Tested in an MTT cell proliferation assay in A549 cells, the inhibitory activities on cancer cell growth for EKB-1, EKB-2, EKB-3, EKB-4, JDB-1, and JDB-2 were found to be 62.2%, 51.5%, 55.5%, 60.5%, 24.6%, and 39.7%, respectively. Again, DMSO treated cells served as the negative control. The glucose uptake inhibition and cell growth inhibition of comparative compound WZB-134 in A549 cells (structure seen below and described in U.S. Pat. No. 9,181,162, which is incorporated by reference herein) is also provided in Table 1.

TABLE 1

| Compound | Glucose Uptake Inhibition in A549 Cells (at 30 μM) | Cell Growth Inhibition in A549 Cells (at 30 μM) |
|---|---|---|
| DMSO | 0% | 0% |
| WZB-134 | 96% | 10% |
| EKB-1 | 54.3% | 62.2% |
| EKB-2 | 56.1% | 51.5% |
| EKB-3 | 62.8% | 55.5% |
| EKB-4 | 77.8% | 60.5% |

TABLE 1-continued

| Compound | Glucose Uptake Inhibition in A549 Cells (at 30 μM) | Cell Growth Inhibition in A549 Cells (at 30 μM) |
|---|---|---|
| JDB-1 | 19.7% | 24.6% |
| JDB-2 | 34.8% | 39.7% |

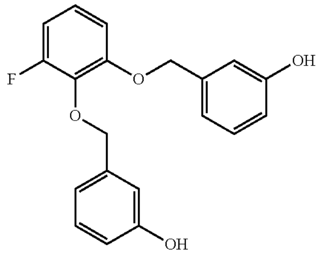

WZB-134

Compounds EKB-3 and EKB-4 were assayed for their ability to inhibit glucose uptake and cell growth in H1299 lung cancer cell lines. A standard glucose uptake assay may be used to evaluate glucose uptake inhibition, and an MTT cell proliferation assay may be used to evaluate cancer cell growth inhibition. As seen in Table 2, both compounds EKB-3 and EKB-4 inhibited basal glucose transport in H1299 cells by 90.5% as measured by a standard glucose uptake assay. DMSO treated cells served as the negative control. Tested in an MTT cell proliferation assay in H1299 cells, the inhibitory activities on cancer cell growth for EKB-3 and EKB-4 were found to be 54% and 50.6%, respectively. Again, DMSO treated cells served as the negative control. The glucose uptake inhibition and cell growth inhibition of comparative compound WZB-134 in H1299 cells is also provided in Table 2.

TABLE 2

| Compound | Glucose Uptake Inhibition in H1299 Cells (at 30 μM) | Cell Growth Inhibition in H1299 Cells (at 30 μM) |
|---|---|---|
| DMSO | 0% | 0% |
| WZB-134 | 92.5% | 10.6% |
| EKB-3 | 90.5% | 54% |
| EKB-4 | 90.5% | 50.6% |

The incorporation of an ester or a hydroxymethyl side chain to one of the benzyl groups, as in compounds EKB-1, EKB-2, EKB-3, EKB-4, JDB-1, and JDB-2, unexpectedly improved cell growth inhibition relative to the unsubstituted ether compound WZB-134. The incorporation of an ester or a hydroxymethyl side chain to one of the benzyl groups may also improve glucose uptake inhibition relative to the unsubstituted ether compounds, such as WZB-134.

In one exemplary embodiment, a method of treating cancer in a subject is provided. The method includes administering to a subject in need of such treatment a therapeutically effective amount of a compound according to formula (I), an enantiomer thereof, or a pharmaceutically acceptable salt thereof. In certain embodiments, a compound according to formula (I), an enantiomer thereof, or a pharmaceutically acceptable salt thereof for use in treating cancer is provided. In certain embodiments, a compound according to formula (I), an enantiomer thereof, or a pharmaceutically acceptable salt thereof is used in the manufacture of a medicament for the treatment of cancer.

In certain embodiments, a method of treating cancer in a subject includes administering to a subject in need of such treatment a therapeutically effective amount of compound EKB-1, an enantiomer thereof, or a pharmaceutically acceptable salt thereof. In certain embodiments, compound EKB-1, an enantiomer thereof, or a pharmaceutically acceptable salt thereof for use in treating cancer is provided. In certain embodiments, compound EKB-1, an enantiomer thereof, or a pharmaceutically acceptable salt thereof is used in the manufacture of a medicament for the treatment of cancer.

In certain embodiments, a method of treating cancer in a subject includes administering to a subject in need of such treatment a therapeutically effective amount of compound EKB-2, an enantiomer thereof, or a pharmaceutically acceptable salt thereof. In certain embodiments, compound EKB-2, an enantiomer thereof, or a pharmaceutically acceptable salt thereof for use in treating cancer is provided. In certain embodiments, compound EKB-2, an enantiomer thereof, or a pharmaceutically acceptable salt thereof is used in the manufacture of a medicament for the treatment of cancer.

In certain embodiments, a method of treating cancer in a subject includes administering to a subject in need of such treatment a therapeutically effective amount of compound EKB-3, an enantiomer thereof, or a pharmaceutically acceptable salt thereof. In certain embodiments, compound EKB-3, an enantiomer thereof, or a pharmaceutically acceptable salt thereof for use in treating cancer is provided. In certain embodiments, compound EKB-3, an enantiomer thereof, or a pharmaceutically acceptable salt thereof is used in the manufacture of a medicament for the treatment of cancer.

In certain embodiments, a method of treating cancer in a subject includes administering to a subject in need of such treatment a therapeutically effective amount of compound EKB-4, an enantiomer thereof, or a pharmaceutically acceptable salt thereof. In certain embodiments, compound EKB-4, an enantiomer thereof, or a pharmaceutically acceptable salt thereof for use in treating cancer is provided. In certain embodiments, compound EKB-4, an enantiomer thereof, or a pharmaceutically acceptable salt thereof is used in the manufacture of a medicament for the treatment of cancer.

In one exemplary embodiment, a method of treating cancer in a subject is provided. The method includes administering to a subject in need of such treatment a therapeutically effective amount of a compound according to formula (II), an enantiomer thereof, or a pharmaceutically acceptable salt thereof. In certain embodiments, a compound according to formula (II), an enantiomer thereof, or a pharmaceutically acceptable salt thereof for use in treating cancer is provided. In certain embodiments, a compound according to formula (II), an enantiomer thereof, or a pharmaceutically acceptable salt thereof is used in the manufacture of a medicament for the treatment of cancer.

In certain embodiments, a method of treating cancer in a subject includes administering to a subject in need of such treatment a therapeutically effective amount of compound JDB-1, an enantiomer thereof, or a pharmaceutically acceptable salt thereof. In certain embodiments, compound JDB-1, an enantiomer thereof, or a pharmaceutically acceptable salt thereof for use in treating cancer is provided. In certain embodiments, compound JDB-1, an enantiomer thereof, or a pharmaceutically acceptable salt thereof is used in the manufacture of a medicament for the treatment of cancer.

In certain embodiments, a method of treating cancer in a subject includes administering to a subject in need of such treatment a therapeutically effective amount of compound JDB-2, an enantiomer thereof, or a pharmaceutically acceptable salt thereof. In certain embodiments, compound JDB-2, an enantiomer thereof, or a pharmaceutically acceptable salt thereof for use in treating cancer is provided. In certain embodiments, compound JDB-2, an enantiomer thereof, or a pharmaceutically acceptable salt thereof is used in the manufacture of a medicament for the treatment of cancer.

In one exemplary embodiment, a method of treating cancer in a subject is provided. The method includes administering to a subject in need of such treatment a therapeutically effective amount of a compound according to formula (I), an enantiomer thereof, or a pharmaceutically acceptable salt thereof in combination with a compound according to formula (II), an enantiomer thereof, or a pharmaceutically acceptable salt thereof. In certain embodiments, a combination of a compound according to formula (II), an enantiomer thereof, or a pharmaceutically acceptable salt thereof and a compound according to formula (II), an enantiomer thereof, or a pharmaceutically acceptable salt thereof for use in treating cancer is provided. In certain embodiments, a compound according to formula (II), an enantiomer thereof, or a pharmaceutically acceptable salt thereof and a compound according to formula (II), an enantiomer thereof, or a pharmaceutically acceptable salt thereof are used in the manufacture of a medicament for the treatment of cancer.

In certain embodiments, a method of treating cancer in a subject includes administering to a subject in need of such treatment a therapeutically effective amount of: at least one of compounds EKB-1, EKB-2, EKB-3, and EKB-4, enantiomers thereof, or pharmaceutically acceptable salts thereof; in combination with at least one of compounds JDB-1 and JDB-2, enanatiomers thereof, or pharmaceutically acceptable salts thereof. In certain embodiments, a combination of at least one of compounds EKB-1, EKB-2, EKB-3, and EKB-4, enantiomers thereof, or pharmaceutically acceptable salts thereof; and at least one of compounds JDB-1 and JDB-2, enanatiomers thereof, or pharmaceutically acceptable salts thereof, for use in treating cancer is provided. In certain embodiments, at least one of compounds EKB-1, EKB-2, EKB-3, and EKB-4, enantiomers thereof, or pharmaceutically acceptable salts thereof; and at least one of compounds JDB-1 and JDB-2, enanatiomers thereof, or pharmaceutically acceptable salts thereof, are used in the manufacture of a medicament for the treatment of cancer.

In certain embodiments of the methods and uses disclosed herein, the cancer is a solid malignant tumor that upregulates basal glucose transport via a biological shift from oxidative phosphorylation to glycolysis in a process known as the Warburg effect.

In certain embodiments of the methods and uses disclosed herein, the cancer is selected from lung cancer, colon cancer, melanoma, leukemia, ovarian cancer, renal cancer, prostate cancer, breast cancer, or a glioma.

In certain embodiments of the methods and uses disclosed herein, administration of the compound to a human subject may be by any method selected from the group consisting of oral, topical, intra-arterial, intrapleural, intrathecal, intraventricular, subcutaneous, intraperitoneal, intraveneous, intravesicular, and gliadel wafers.

In certain embodiments of the methods and uses disclosed herein, a compound of formula (I), a compound of formula (II), enantiomers thereof, or pharmaceutically acceptable salts thereof may be administered to a human subject or patient in combination with one or multiple chemotherapeutic agents as a means to enhance the efficacy of one or more of the therapeutically useful compounds. Accordingly, in certain embodiments of the methods and uses disclosed herein, the methods and uses may further include administering to the subject in need of such treatment a second cancer drug.

In certain embodiments of the methods and uses disclosed herein, a compound of formula (I), a compound of formula (II), enantiomers thereof, or pharmaceutically acceptable salts thereof may be administered to a human subject or patient in combination with a chemotherapeutic agent selected from the group consisting of methotrexate, doxorubicin hydrochloride, fluorouracil, everolimus, imiquimod, aldesleukin, alemtuzumab, pemetrexed disodium, palonosetron hydrochloride, chlorambucil, aminol evulinic acid, anastrozole, aprepitant, exemestane, nelarabine, arsenic trioxide, ofatumumab, bevacizumab, azacitidine, bendamustine hydrochloride, bexarotene, bleomycin, bortezomib, cabazitaxel, irinotecan hydrochloride, capecitabine, carboplatin, daunorubicin hydrochloride, cetuximab, cisplatin, cyclophosphamide, clofarabine, Ifosfamide, cytarabine, dacarbazine, decitabine, dasatinib, degarelix, denileukin difitox, denosumab, dexrazoxane hydrochloride, docetaxel, rasburicase, epirubicin hydrochloride, oxaliplatin, eltrombopaq olamine, eribulin mesylate, erlotinib hydrochloride, etoposide phosphate, raloxifene hydrochloride, toremifane, fulvestrant, letrozole, filgrastim, fludarabim phosphate, pralatrexate, gefitinib, gemcitabine hydrochloride, gemcitibine-cisplatin, gemtuzumab ozogamicin, imatinib mesylate, trastuzamab, topotecan hydrochloride, ibritumomab tiuxetan, romadepsin, ixabepilone, palifermin, lapatinib ditosylate, lenalidomide, leucovorin calcium, leuprolide acetate, liposomal procarbazine hydrochloride, temozolomide, plerixafor, acetidine, sorafenib tosylate, nilotinib, tamoxifen citrate, romiplostim, paclitaxel, pazopanib hydrochloride, pegaspargase, prednisone, procarbazine hydrochloride, proleukin, rituximab, romidepsin, Talc, sorafenic tosylate, sunitinib malate, thalidomide, temsirolimus, toremifene, trastuzumub, pantiumumab, vinblastine sulfate, vincristine, vorinostat, and zoledronic acid.

Although several exemplary compounds that inhibit or reduce glucose transport and methods of using the chemical compounds to treat cancer have been described herein, it should be appreciated that many modifications can be made without departing from the spirit and scope of the present disclosure. All such modifications are intended to be included within the scope of the present disclosure and are to be limited only by the following claims.

What is claimed is:

1. A compound according to formula (I), an enantiomer thereof, or a salt thereof:

Formula (I)

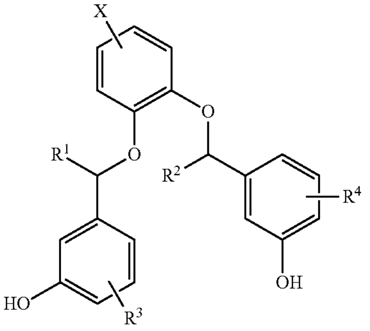

wherein X is selected from the group consisting of: halogen; hydrogen; —O-alkyl; hydroxyl (—OH); azido (—$N_3$); cyano (—CN); nitro (—$NO_2$); and methoxycarbonyl (—$CO_2Me$);

wherein $R^1$ and $R^2$ are independently selected from the group consisting of:

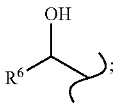

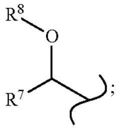

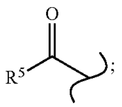

and hydrogen;

wherein $R^3$ and $R^4$ are independently selected from the group consisting of: hydrogen; halogen; alkyl; —O-alkyl; hydroxyl (—OH); cyano (—CN); and methoxycarbonyl (—$CO_2Me$);

wherein one of $R^1$ and $R^2$ is hydrogen;

wherein $R^6$ is selected from the group consisting of: hydrogen; alkyl; and aryl;

wherein $R^5$ is selected from the group consisting of: hydroxyl (—OH); —O-alkyl; —NH-alkyl; and —N-$(alkyl)_2$;

wherein $R^7$ is selected from the group consisting of: alkyl; aryl; and heteroaryl and wherein $R^8$ is selected from the group consisting of: alkyl; aryl; and heteroaryl.

2. The compound according to claim 1, wherein:

X is halo;

$R^1$ is hydrogen;

$R^2$ is

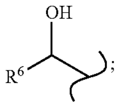

$R^3$ is hydrogen;

$R^4$ is hydrogen; and $R^6$ is hydrogen.

3. The compound according to claim 2, wherein X is —Cl.

4. The compound according to claim 1, wherein:

X is halo;

$R^1$ is

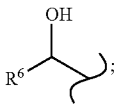

$R^2$ is hydrogen;

$R^3$ is hydrogen;

$R^4$ is hydrogen; and $R^6$ is hydrogen.

5. The compound according to claim 4, wherein X is —Cl.

6. The compound according to claim 1, wherein:

X is halo;

$R^1$ is hydrogen;

$R^2$ is

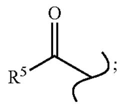

$R^3$ is hydrogen;

$R^4$ is hydrogen; and $R^5$ is —O-alkyl.

7. The compound according to claim 6, wherein:

X is —Cl; and $R^5$ is methoxy (—OMe).

8. The compound according to claim 1, wherein:

X is halo;

$R^1$ is

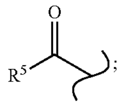

$R^2$ is hydrogen;

$R^3$ is hydrogen;

$R^4$ is hydrogen; and $R^5$ is —O-alkyl.

9. The compound according to claim 8, wherein:

X is —Cl; and $R^5$ is methoxy (—OMe).

10. A compound according to formula (II), an enantiomer thereof, or a salt thereof:

Formula (II)

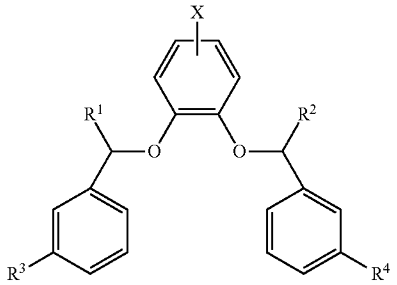

wherein X is selected from the group consisting of: hydrogen; halogen; —O-alkyl; hydroxyl (—OH); cyano (—CN); azido (—$N_3$); nitro (—$NO_2$); and methoxycarbonyl (—$CO_2Me$);

wherein $R^1$ and $R^2$ are independently selected from the group consisting of: hydrogen; hydroxymethyl (—$CH_2OH$); and methoxycarbonyl (—$CO_2Me$);

wherein one of $R^1$ and $R^2$ is hydrogen;

wherein when $R^1$ is hydrogen, $R^3$ is hydroxyl (—OH) and $R^4$ is —O-alkyl; and wherein when $R^2$ is hydrogen, $R^3$ is —O-alkyl and $R^4$ is hydroxyl (—OH).

11. The compound according to claim 10, wherein:

X is halo;

$R^1$ is hydrogen;

$R^2$ is methoxycarbonyl (—$CO_2Me$);

$R^3$ is hydroxyl (—OH); and $R^4$ is —O-alkyl.

12. The compound according to claim 11, wherein:

X is —Cl; and $R^4$ is methoxy (—OMe).

13. The compound according to claim 10, wherein:

X is halo;

$R^1$ is hydrogen;

$R^2$ is hydroxymethyl (—$CH_2OH$);

$R^3$ is hydroxyl (—OH); and $R^4$ is —O-alkyl.

14. The compound according to claim 13, wherein:

X is —Cl; and $R^4$ is methoxy (—OMe).

15. A method of treating lung cancer in a subject comprising:

administering to a subject in need of such treatment a therapeutically effective amount of a compound according to formula (I), an enantiomer thereof, or a salt thereof:

Formula (I)

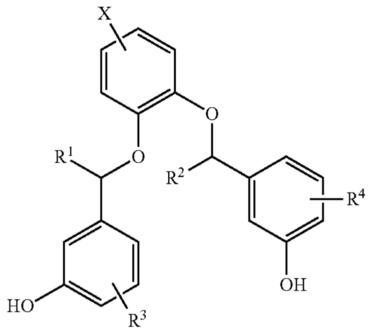

wherein X is selected from the group consisting of: halogen; hydrogen; —O-alkyl; hydroxyl (—OH); azido (—$N_3$); cyano (—CN); nitro (—$NO_2$); and methoxycarbonyl (—$CO_2Me$);

wherein $R^1$ and $R^2$ are independently selected from the group consisting of:

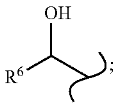

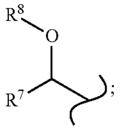

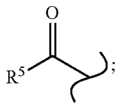

and hydrogen;

wherein $R^3$ and $R^4$ are independently selected from the group consisting of: hydrogen; halogen; alkyl; —O-alkyl; hydroxyl (—OH); cyano (—CN); and methoxycarbonyl (—$CO_2Me$);

wherein one of $R^1$ and $R^2$ is hydrogen;

wherein $R^6$ is selected from the group consisting of: hydrogen; alkyl; and aryl;

wherein $R^5$ is selected from the group consisting of: hydroxyl (—OH); —O-alkyl; —NH-alkyl; and —N-$(alkyl)_2$;

wherein $R^7$ is selected from the group consisting of: alkyl; aryl; and heteroaryl and wherein $R^8$ is selected from the group consisting of: alkyl; aryl; and heteroaryl.

16. The method according to claim 15, wherein the compound is

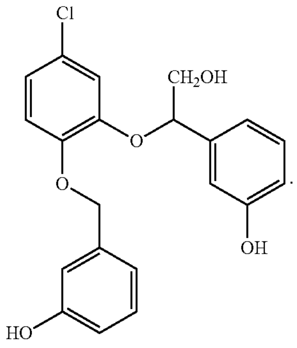 [SMILES: OCC(Oc1cc(Cl)ccc1OCc1cccc(O)c1)c1cccc(O)c1]

17. A method of treating lung cancer in a subject comprising:

administering to a subject in need of such treatment a therapeutically effective amount of a compound according to formula (II), an enantiomer thereof, or a salt thereof:

Formula (II)

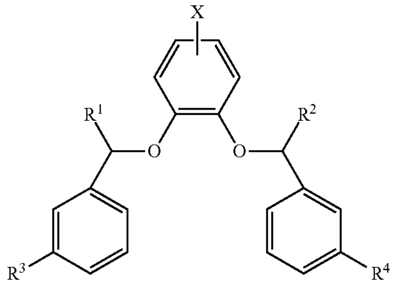

wherein X is selected from the group consisting of: hydrogen; halogen; —O-alkyl; hydroxyl (—OH); cyano (—CN); azido (—$N_3$); nitro (—$NO_2$); and methoxycarbonyl (—$CO_2$Me);

wherein $R^1$ and $R^2$ are independently selected from the group consisting of: hydrogen; hydroxymethyl (—$CH_2$OH); and methoxycarbonyl (—$CO_2$Me);

wherein one of $R^1$ and $R^2$ is hydrogen;

wherein when $R^1$ is hydrogen, $R^3$ is hydroxyl (—OH) and $R^4$ is —O-alkyl; and wherein when $R^2$ is hydrogen, $R^3$ is —O-alkyl and $R^4$ is hydroxyl (—OH).

18. The method according to claim 17, wherein:

X is halo;

$R^1$ is hydrogen;

$R^2$ is methoxycarbonyl (—$CO_2$Me);

$R^3$ is hydroxyl (—OH); and $R^4$ is —O-alkyl.

19. The method according to claim 17, wherein:

X is halo;

$R^1$ is hydrogen;

$R^2$ is hydroxymethyl (—$CH_2$OH);

$R^3$ is hydroxyl (—OH); and $R^4$ is —O-alkyl.

* * * * *